United States Patent
Katz et al.

[11] Patent Number: 6,002,965
[45] Date of Patent: Dec. 14, 1999

[54] SELF APPLIED DEVICE AND METHOD FOR PREVENTION OF DEEP VEIN THROMBOSIS

[76] Inventors: Amiram Katz; Orly Katz, both of 15 Beaver Brook Rd., Weston, Conn. 06470

[21] Appl. No.: 09/094,512

[22] Filed: Jun. 10, 1998

[51] Int. Cl.[6] .............................. A61N 1/24; A61N 1/22; A61N 1/18
[52] U.S. Cl. .............................. 607/48; 607/63; 607/72; 128/DIG. 15
[58] Field of Search .................. 607/48, 63, 72, 607/76; 128/DIG. 15

[56] References Cited

U.S. PATENT DOCUMENTS

| | | | |
|---|---|---|---|
| 3,472,233 | 10/1969 | Sarbacher | 607/48 |
| 4,157,087 | 6/1979 | Miller et al. . | |
| 4,759,368 | 7/1988 | Spanton et al. . | |
| 5,342,410 | 8/1994 | Braverman . | |
| 5,358,513 | 10/1994 | Powell, III et al. . | |
| 5,487,759 | 1/1996 | Bastyr et al. | 607/46 |
| 5,628,722 | 5/1997 | Solomonow et al. | 607/48 |
| 5,643,331 | 7/1997 | Katz . | |
| 5,674,262 | 10/1997 | Tumey . | |
| 5,782,893 | 7/1998 | Dennis, III . | |

FOREIGN PATENT DOCUMENTS

| | | |
|---|---|---|
| 39 16994 A1 | 11/1990 | Germany . |
| 703101 | 12/1979 | U.S.S.R. . |

OTHER PUBLICATIONS

Hirsh, MD et al; Prevalence of Deep Venous Thrombisis Amung Patients in Medical Intensive Care; JAMA, Jul. 26, 1995; vol. 274, No. 4, pp. 335–337.

Pambianco, MS, MPH, et al; Deep Vein Thrombosis; Prevention in Sroke Patients During Rehabilitation; Arch Phys Med Rehabil, vol. 76, Apr. 1995; pp. 324–330.

Klecker und W. Theiss; Die transkutane elektrische Muskelstimulation–eine Neue Moglichkeit zur Thrombosephophylaxe?; VASA Band 23, Heft 1; pp. 23–29.

Anderson Jr. PhD, et al; A Population Based Perspective of the Hospital Incidence and Case Fatality Rates of Deep Vein Thrombosis and Pulmonary Embolism; Arch Intern Med, vol. 151, May 1991; pp. 933–938.

R. Sarvesvaran; Sudden Natural Deaths Associated with Air Travel; Med. Sci. Law; vol. 26, No. 1; 1986; pp. 35–38.

J. Winkel; Swelling of the Lower Leg in Sedentary Work–A Pilot Study; J. Human Ergol, 10; 1981; pp. 139–149.

*Primary Examiner*—William E. Kamm
*Assistant Examiner*—Carl H. Layno
*Attorney, Agent, or Firm*—Fattibene & Fattibene; Paul A. Fattibene; Arthur T. Fattibene

[57] ABSTRACT

An elongated rectangular cuff having fasteners and electrodes with an attached control unit for providing a predetermined electrical signal to the electrodes. The predetermined electrical signal is substantially a square wave with a duration of between 0.1 and 0.3 milliseconds, a frequency of between 0.1 and 0.5 Hertz, with 5 to 15 repetitions delivered every 5 to 15 minute intervals. The control unit provides a controllable intensity of between 1 to 20 milliamperes. The cuff or sleeve, when wrapped around a user's leg and positioned below the knee such that the electrodes contact the calf muscles, causes a muscle and nerve stimulation resulting in contraction of the calf muscle. Blood flow is therefore increased regardless of body position or a movement greatly decreasing the possibility of developing deep vein thrombosis or pulmonary embolism, which may be fatal. In addition it reduces ankle edema and leg discomfort associated with prolonged sitting. A predetermined applied signal is safe with little risk of harm to the user. Additionally, preferably the control unit has a single external control for controlling intensity preventing a user from applying an inappropriate signal. A simple to use, compact device and method is disclosed that can safely be used by individuals having no prior knowledge of anatomy, effectively during extended periods of sitting or immobility, such as when traveling.

18 Claims, 4 Drawing Sheets

6,002,965

SELF APPLIED DEVICE AND METHOD FOR PREVENTION OF DEEP VEIN THROMBOSIS

FIELD OF THE INVENTION

This invention relates to an electronic stimulator, and more specifically to an electronic nerve and muscle stimulator and method useful for preventing venous thrombo embolism, venostasis, varicose veins, ankle edema, and leg discomfort resulting from prolonged sitting that can be self administered by a patient.

BACKGROUND OF THE INVENTION

There are a large number of diagnosed cases of deep vein thrombosis, DVT, in the United States annually. There are also a large number of fatal cases of pulmonary embolism, PE, many of which can be prevented with appropriate measures, such as pharmacological or mechanical. Prolonged sitting, such as when traveling or working long hours, can aggravate or promote DVT or PE. It can also cause ankle edema and leg discomfort. Studies have indicated that about one-fifth of the sudden natural deaths associated with commercial air travel that were brought to the London Coroner from Heathrow Airport were due to pulmonary embolism. There is a need for a device that helps to stimulate blood flow so as to prevent DVT and PE during the above mentioned circumstances. One such device is disclosed in U.S. Pat. No. 5,643,331 entitled "Method and Device For Prevention of Deep Vein Thrombosis" issuing to Katz on Jul. 1, 1997, which is herein incorporated by reference. Therein disclosed is an electrical stimulator generating a square wave pattern having a controllable duration ranging from 0.1 to 0.3 milliseconds, a controllable frequency ranging between 0.001 to 0.5 cycles per second, and a controllable intensity ranging from 1 to 20 milliamperes. An electrode is positioned externally at or near the tibial nerve at the popliteal fossa to deliver the electrical signal. This signal stimulates the nerve, causing a muscle contraction which helping to stimulate blood flow. The increased blood flow helps in preventing deep vein thrombosis, ankle edema, and venostasis. Additionally, there are numerous transcutaneous electric nerve stimulating devices, TENS units, used to control pain. There are also similar muscle and neurological stimulating devices, MANS units, also used to control or manage pain. All of these devices deliver relatively high frequency stimuli, for example 25 to 50 Hertz. They are generally not tolerated well by patients, especially when used for relatively long periods of time. Additionally, these devices are not completely suitable for the prevention of DVT or PE. Accordingly, while these units used for pain management or control are similar, they are not suited to relatively long term use and self-application by a patient for the prevention of DVT, PE ankle edema and leg discomfort. Therefore, there is a need for a device and method of application that can easily be self-administered by a patient during extended periods of sitting or inactivity, for example during traveling in a car or a plane, or sitting for many hours while working to help prevent DVT, PE ankle edema and leg discomfort.

SUMMARY OF THE INVENTION

The present invention comprises a self-contained electrical device having pre-positioned electrodes making it easy to be self-applied by a patient and worn for extended periods of time during periods of inactivity or immobility, such as when paralyzed, hospitalized or sitting during traveling or working. An elongated rectangular cuff or sleeve has straps and strips of hook and loop fastener material. Two electrodes having a predetermined position are connected to a control unit. Indicia or marking on the sleeve is placed between the two electrodes to aid in the proper positioning of the electrodes onto the leg of a patient or user. The indicia helps the user to position the electrodes without any specific knowledge of anatomy. The cuff or sleeve is sized to wrap around the calf of a user and to be securely held thereto in a proper predetermined position. The control unit attached to the cuff is preset to provide a substantially square wave signal to the electrodes having a duration of 0.3 milliseconds, a frequency of 0.1 to 0.5 Hertz with 5 to 15 repetitions delivered every 5 to 15 minutes. The control unit has a structure permitting a user to control intensity only, and only within a range of 1 to 20 milliamperes. The intensity control is the only user controlled adjustment.

Accordingly, it is an object of the present invention to provide a device that can be user applied and operated safely.

It is a further object of the present invention to provide a small, self-contained electronic stimulator for generating an effective muscle contraction of the calves by externally stimulating the muscle.

It is an advantage of the present invention that it is self-contained and can usually be placed into a predetermined position by a user.

It is a further advantage of the present invention that it can be worn under the clothes.

It is yet another advantage of the present invention that it can be worn over hosiery up to twenty-five denier.

It is a feature of the present invention that a square wave is applied having a duration of 0.3 milliseconds, a frequency of 0.1 to 0.5 Hertz, with 5 to 15 repetitions delivered every 5 to 15 minutes with a user controllable intensity of 1 to 20 milliamperes.

It is another feature of the present invention that it has a single control adjusted by the user for controlling intensity only.

These and other objects, advantages, and features will become readily apparent in view of the following detailed description.

DETAILED DESCRIPTION OF THE PREFERRED EMBODIMENTS

Figure 1:
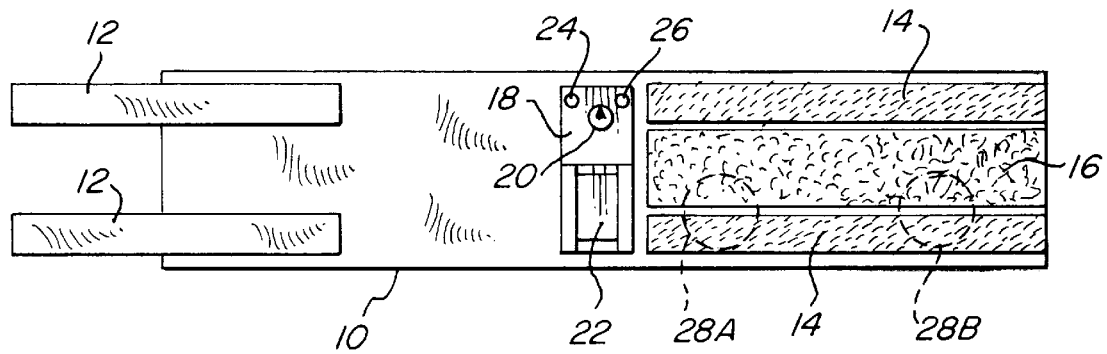
FIG. 1 is a plan view of one side of the present invention.

FIG. 1 is a plan view illustrating one embodiment of the present invention. An elongated rectangular sleeve or cuff 10 is made of a material, preferably an elastic type material. On one end thereof are positioned straps 12. At the other end thereof are positioned complimentary strips 14. The straps 12 and the strips 14 have complimentary hook and loop fasteners such as those sold under the trademark VELCRO. Between the strips 14 is placed a patch 16. Patch 16 is made of a hook or loop fastener material. Approximately at the longitudinal center of the cuff or sleeve 10 is positioned a control unit 18. Control unit 18 has an on-off intensity or amplitude knob 20, a power supply or battery 22, a low battery indicator 24, and an on-off indicator 26. The control unit 18 provides a square wave signal to electrodes 28A and 28B. The electrodes 28A and 28B are placed at a predetermined position so as to provide proper anatomical placement. The substantially square wave signal preferably has a duration of 0.3 milliseconds, a frequency of 0.1 to 0.5 Hertz, with 5 to 15 repetitions delivered every 5 to 15 minutes with a user controllable intensity of between 1 to 20 milliamperes. The on-off intensity knob 20 is the only external control, and controls the amplitude of the applied square wave signal in milliamperes. The elongated rectangular sleeve or cuff 10 has a longitudinal dimension of approximately sixty centimeters and a lateral dimension of approximately fifteen centimeters.

Figure 2:
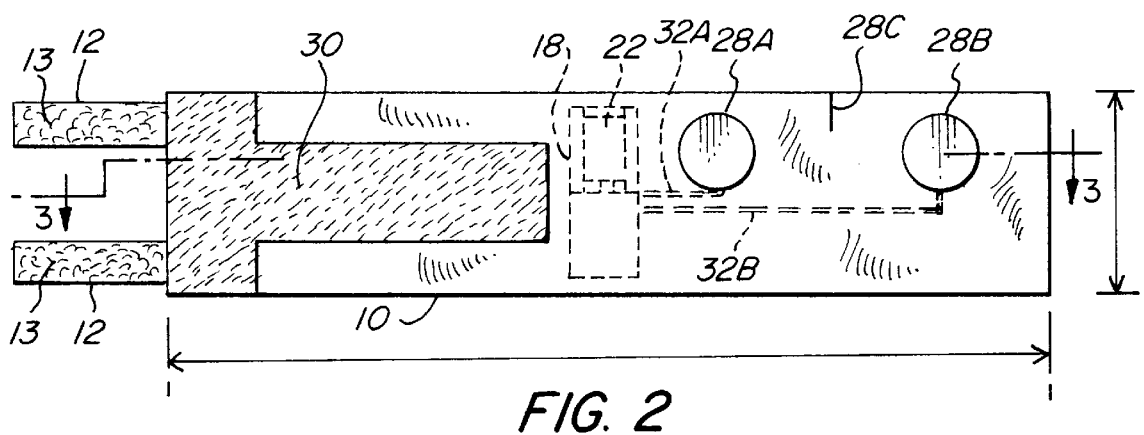
FIG. 2 is a plan view of another side of the present invention.

FIG. 2 is a plan view illustrating the other planar side of the cuff or sleeve 10. This side is placed adjacent the calf of a user. A patch 30 of loop material is placed adjacent the straps 12 having a hook type material 13 thereon. Electrodes 28A and 28B are separated by a distance ranging between seven and seventeen centimeters. Preferably, the distance between centers of the electrodes 28A and 28B is twelve centimeters. An indicia line 28C is placed midway between the electrodes 28A and 28B as a guide for positioning the electrodes 28A and 28B on the leg of a user. Wires or electrical conductors 32A and 32B are connected to their respective electrodes 28A and 28B, and the control unit 18. The electrodes 28A and 28B may be any conventional electrode, and are preferably of a disposable type that is adhesively attached to the skin. Connectors may be utilized for detaching and attaching electrodes 28A and 28B to the wires or electrical conductors 32A and 32B.

Figure 3:
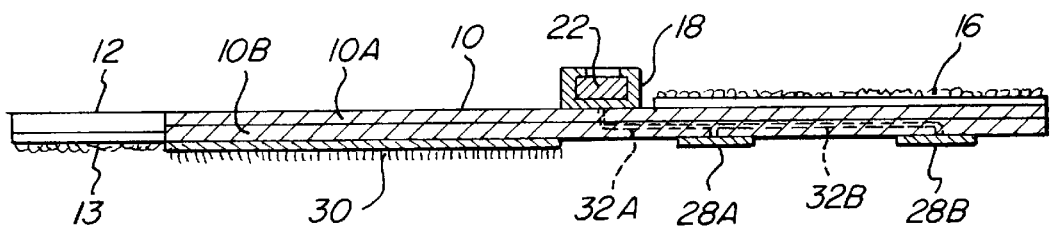
FIG. 3 is a cross section taken along line 3—3 in FIG. 2.

FIG. 3 is a cross section taken along line 3—3 in FIG. 2. The sleeve or cuff 10 is made of a first layer of material 10A and a second layer of material 10B. Attached to the first layer of material 10A is the control unit 18. The control unit 18 may also be placed in a fabric pouch, not shown, attached to the first layer of material 10A. Between the first layer of material 10A and the second layer of material 10B are placed wires or electrical conductors 32A and 32B. Electrodes 28A and 28B are attached to the second material 10B. The electrodes 28A and 28B are preferably replaceable and made of a disposable electrode. Any other equivalent type electrode may be used. Patch 30 is made of a loop type or pile material that complements, or mate with, or attaches to patch 16 which is made of a hook type material. Additionally, straps 12 have a hook type material 13 thereon which is designed to mate with or attach to the strips 14 made of a loop type material illustrated in FIG. 1. Accordingly, the sleeve 10 may be securely wrapped and held in position around a leg of a user. The cuff or sleeve 10 is easily adjustable for comfort as well as adaptability to different users.

Figure 4:
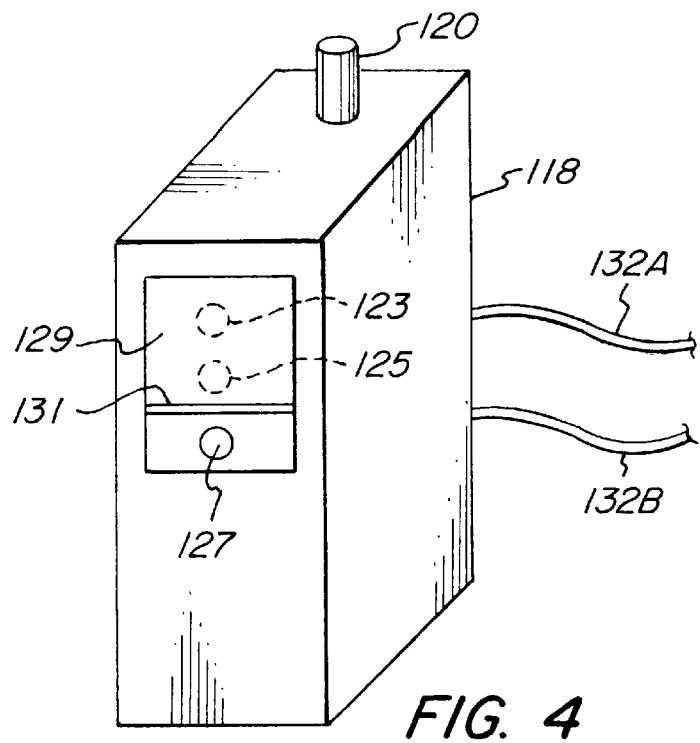
FIG. 4 is a perspective view of another embodiment of a control unit.

FIG. 4 is a perspective view of another control unit that may be utilized with the cuff or sleeve 10 illustrated in FIGS. 1–3. The control unit 118 has a single on-off intensity or amplitude knob 120. Additionally, a sliding door 129 having a handle 131 covers a repetition control 123, a frequency control 125, and an interval control 127. These controls are normally covered by door 129, permitting the user to access only the on-off intensity amplitude knob 120. However, the door 129 may be opened to gain access to additional controls for adjusting the electrical signal applied to the electrodes by wires or conductors 132A and 132B. For example, frequency control 125 may control the period or space between the train of square waves, and repetition control 123 may control the number of square waves delivered in the train of square waves, and interval control 127 may control the time period between the plurality of square wave repetitions or square wave train. Accordingly, the control unit 118 illustrated in FIG. 4 provides a more flexible means for adjusting the control unit. In the control unit illustrated in FIGS. 1–3, the control unit 18 has only one external adjustment, with the other adjustments being fixed or internally controlled. Accordingly, the use of the present invention is greatly simplified for the user, and helps prevents the user from generating a potentially harmful signal.

Figure 5:
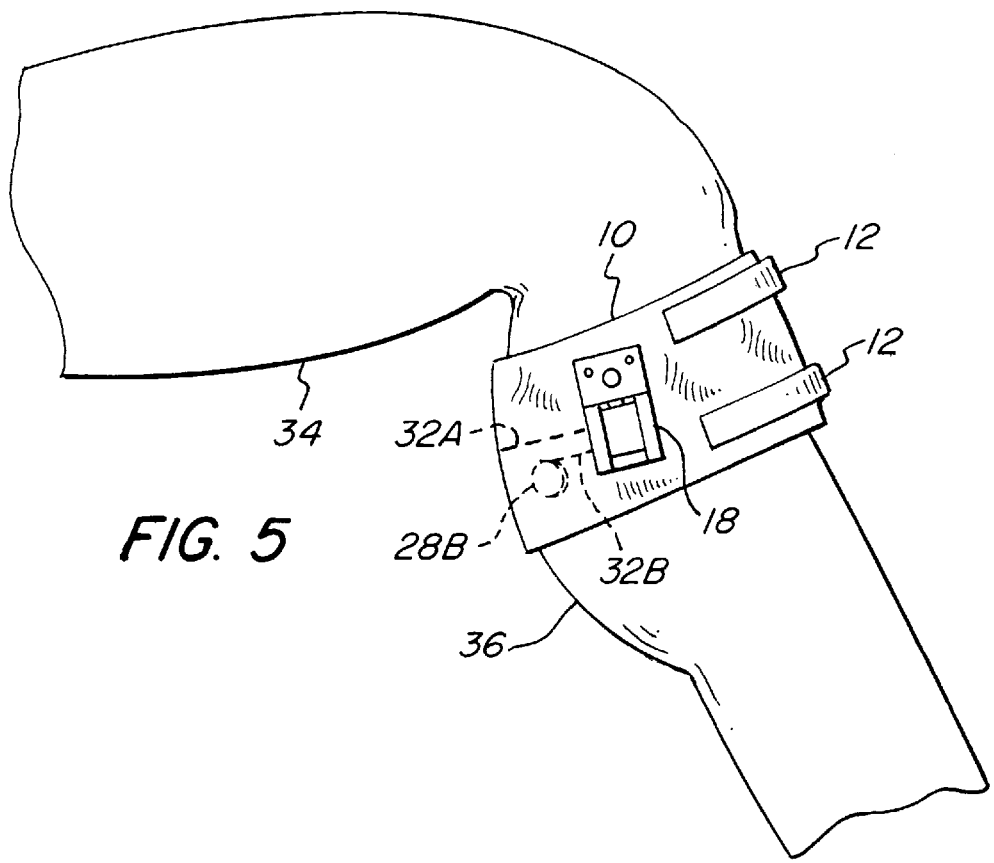
FIG. 5 schematically illustrates the placement of the present invention on the calf of a user.

FIG. 5 illustrates the placement and use of the present invention on the calf of a user. The cuff or sleeve 10 is wrapped around the user's calf 36 of the user's leg 34. Straps 12 are used to securely hold the sleeve 10 in place. The midline indicia 28C, illustrated in FIG. 2, is positioned in the midback of the upper calf 36. The cuff 10 is preferably positioned approximately five centimeters below the crease behind the kneecap. The electrodes 28B and 28A, not illustrated in FIG. 5, are thereby properly positioned to stimulate the calf muscle with a predetermined signal.

Figure 6:
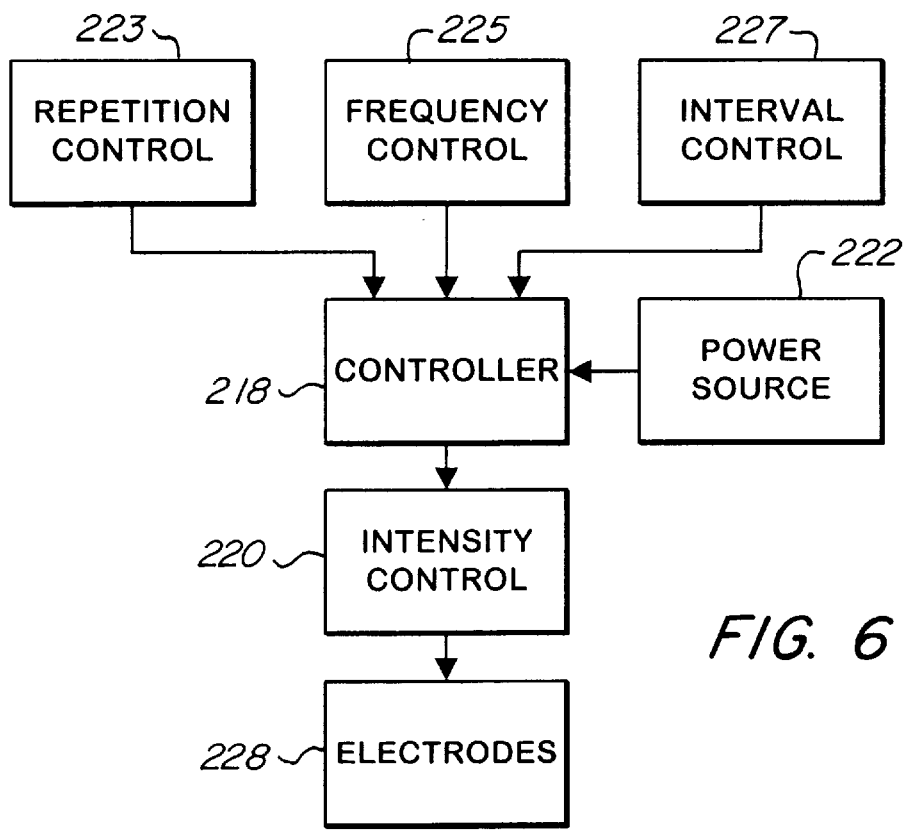
FIG. 6 is a block diagram illustrating the method of operation of the present invention.

FIG. 6 is a block diagram illustrating the operation of the present invention. A repetition control 223, frequency control 225, and interval control 227 are coupled to a controller 218. A power source 222 provides power to the controller. The controller is coupled to an intensity control 220 which provides a square wave to electrodes 228.

Figure 7:
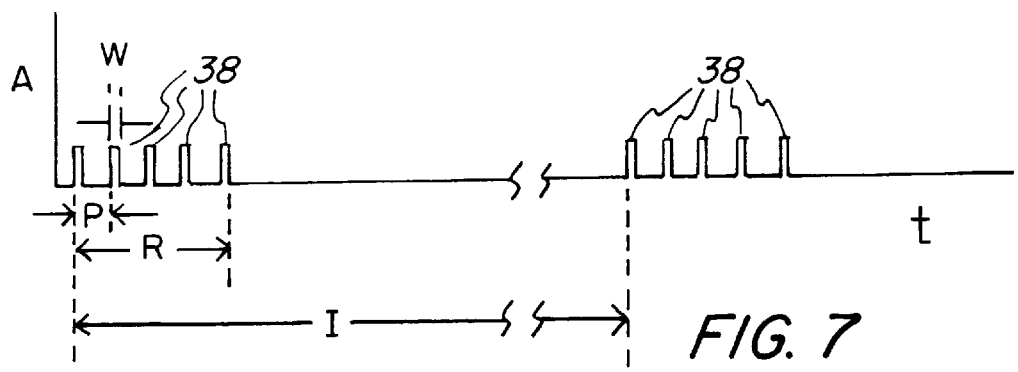
FIG. 7 is a graph illustrating a signal according to the present invention.

FIG. 7 is a graph illustrating the wave form or signals provided to the electrodes in the present invention. The control unit 18, illustrated in FIGS. 1–3, produces a train of substantially square waves 38 which may be asymmetrical bi-phasic square pulses having a duration or width W of approximately 0.3 milliseconds. Between each pulse or square wave 38 is a period P which results in a frequency between 0.1 and 0.5 Hertz. The square wave train or pulse train generally has a plurality of repetitions R. The plurality of repetitions R of square waves 38 range between five to fifteen square waves 38 in a single train. Each of the square waves 38 has an amplitude of approximately between 1 to 20 milliamperes. The wave train of square waves 38 having a repetition R is repeated at an interval I. The interval I is between five to fifteen minutes. This particular application of a signal to the electrodes placed on the calf muscle is particularly advantageous, because of its relatively low frequency and relatively long duration. In Doppler studies of deep femoral vein blood flow, it has been found that the present invention results in a three to four-fold increase of deep femoral vein blood flow, regardless of body position. This increased flow has been shown to be effective in preventing DVT and PE. Additionally, the present invention is effective in reducing ankle edema and leg discomfort that follows prolonged sitting or immobility.

Figure 7A:
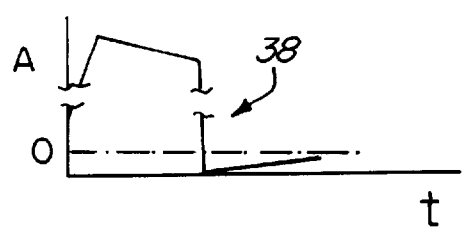
FIG. 7A is a graph illustrating an enlarged wave form of a representative signal.

FIG. 7A is a graph more clearly illustrating an enlarged substantially square wave 38 or an asymmetrical bi-phasic square pulse that is preferably used in the present invention.

Figure 8:
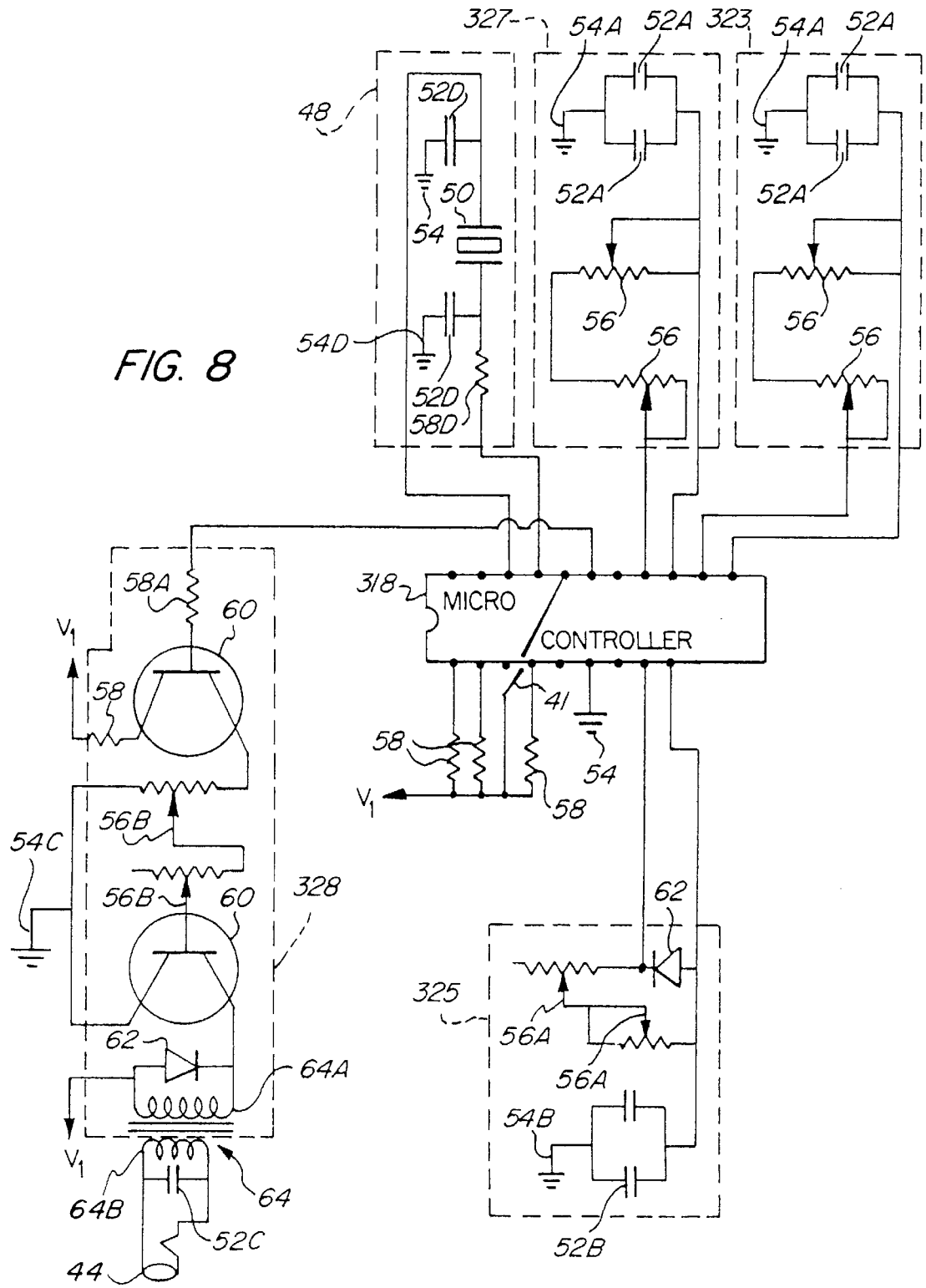
FIG. 8 is a schematic of a representative electrical circuit.

FIG. 8 is a schematic illustrating a representative circuit that may be used to provide the electrical signal of the present invention. The circuit illustrated in FIG. 8 is only meant to be a representative circuit, whereas other equivalent circuits may be derived by those skilled in the art, in following the teachings of the present invention.

The circuit illustrated in FIG. 8 can be divided into general functional portions, for example, portion 48 illustrates an oscillator, portion 327 illustrates an interval control, portion 323 illustrates a repetition control, portion 325 illustrates a frequency control, and portion 328 illustrates an electrode control. Each of the portions 48, 327, 323, 325, and 328 are coupled to a microprocessor, CPU, or controller 318. The controller 318 is powered by an input voltage $V_1$. $V_1$ may be provided by any power source such as a rechargeable battery or a nine-volt battery. The input voltage $V_1$ is coupled to the controller 318 through resistors 58 and a switch 41. The controller 318 is also connected to ground 54. The interval control portion 327 comprises a pair of variable resistors 56 and a pair of capacitors 52A. One electrode of the respective capacitors 52A is connected to a ground 54A. The repetition control portion 323 has an electrical structure similar to the interval portion 327 with variable resistors 56 and capacitors 52A and ground 54A. The frequency control portion 325 comprises a pair of variable resistors 56A, a diode 62 and a pair of capacitors 52B. One of the electrodes for each of the respective capacitors of the pair of capacitors 52B is coupled to ground 54B. The other electrodes for each respective capacitor of the pair of capacitors 52B is coupled to the controller 318. The electrode control portion 328 includes resistors 58 and 58A, transistors 60, variable resistor 56B, which functions as the intensity control, diode 62, and the primary 64A of transformer 64. The electrode portion 328 is also coupled to ground 54C and input voltage $V_1$. Secondary 64B of transformer 64 is coupled to an output jack 44. Capacitor 52C is connected in parallel with secondary 64B of transformer 64. Oscillator portion 48 includes a crystal 50, a resistor 58D, and capacitors 52D. One electrode of each of the capacitors 52D is connected to ground 54D. Jack 44 is connected to the two electrodes 28A and 28B illustrated in FIGS. 1–3.

From the above, it should be readily appreciated that the present invention provides a relatively easy, convenient and safe device and method for applying an electrical signal having a predetermined wave form to the calf muscles of a user's leg. The predetermined electrical signal is advantageous in providing a safe level of stimuli to a user's leg. This stimuli causes muscle contraction which stimulates blood flow, effectively reducing the threat of DVT or PE. It should reduce ankle edema and leg discomfort associated with prolonged sitting. Accordingly, the present invention may be carried by a user and applied with very little to no risk of injury, and requires no prior knowledge of anatomy. When used properly, the present invention will help to prevent many deaths due to DVT and PE among travelers and other immobile or high risk patients.

While the present invention has been described with respect to particular embodiments, variations and modifications may be made without departing from the spirit and scope of this invention.

What is claimed is:

1. A self applied device for use in preventing circulatory ailments comprising:

a rectangular cuff;

a fastening material placed on one end of said rectangular cuff;

a mating fastening material placed on another end of said rectangular cuff, said mating fastening material adapted to attach to said fastening material;

a pair of electrodes positioned a predetermined distance apart and held by said rectangular cuff;

a control unit placed on said rectangular cuff and attached to said pair of electrodes; and a power source attached to said control unit, said fastening material comprises two straps attached to one side of one end of said rectangular cuff, each of said two straps having a first type of fastening material thereon, a first patch of fastening material placed between said two straps and on the other side of said rectangular cuff on the one end, said first patch of fastening material made of a second type of fastening material, the second type of fastening material attaching to the first type of fastening material upon contact; and said mating fastening material comprises two strips attached to the other end of said rectangular cuff on the one side, each of said two strips having the second type of fastening material thereon, a second patch of fastening material placed between said two strips, said second patch of fastening material made of a first type of fastening material, the first type of fastening material attaching to the second type of fastening material upon contact, whereby said rectangular cuff can be easily and securely wrapped around the leg of a user and a user can attach and position the device easily and apply a safe and effective electrical signal causing muscle contraction.

2. A self applied device for use in preventing circulatory ailments comprising:

a rectangular cuff;

a fastening material placed on one end of said rectangular cuff;

a mating fastening material placed on another end of said rectangular cuff, said mating fastening material adapted to attach to said fastening material;

a pair of electrodes positioned a predetermined distance apart and held by said rectangular cuff, the predetermined distance apart of said pair of electrodes is between seven and seventeen centimeters;

a control unit placed on said rectangular cuff and attached to said pair of electrodes;

a power source attached to said control unit, whereby a user can attach and position the device easily and apply a safe and effective electrical signal causing muscle contraction.

3. A self applied device for use in preventing circulatory ailments as in claim 2 wherein:

the predetermined distance apart of said pair of electrodes is approximately twelve centimeters.

4. A self applied device for use in preventing circulatory ailments as in claim 2 further comprising:

an external user adjustable intensity control on said control unit.

5. A self applied device for use in preventing circulatory ailments as in claim 2 wherein:

said power source comprises a battery contained within said control unit.

6. A self applied device for use in preventing circulatory ailments comprising:

a rectangular cuff;

a fastening material placed on one end of said rectangular cuff;

a mating fastening material placed on another end of said rectangular cuff, said mating fastening material adapted to attach to said fastening material;

a pair of electrodes positioned a predetermined distance apart and held by said rectangular cuff;

indicia placed on said rectangular cuff midway between said pair of electrodes, whereby said indicia aids in the proper placement of said pair of electrodes on the leg of a user;

a control unit placed on said rectangular cuff and attached to said pair of electrodes; and a power source attached to said control unit, whereby a user can attach and position the device easily and apply a safe and effective electrical signal causing muscle contraction.

7. A self applied device for use in preventing circulatory ailments comprising:

a rectangular cuff;

a fastening material placed on one end of said rectangular cuff;

a mating fastening material placed on another end of said rectangular cuff, said mating fastening material adapted to attach to said fastening material;

a pair of electrodes positioned a predetermined distance apart and held by said rectangular cuff;

a control unit placed on said rectangular cuff and attached to said pair of electrodes, said control unit provides an electrical signal to said electrodes having a form of substantially a square wave with an intensity of between 1 to 20 milliamperes, a duration of between 0.1 and 0.3 milliseconds, a frequency of between 0.1 and 0.5 Hertz, with 5 to 15 repetitions delivered every 5 to 15 minute intervals; and a power source attached to said control unit, whereby a user can attach and position the device easily and apply a safe and effective electrical signal causing muscle contraction.

8. A self applied device for use in preventing circulatory ailments comprising:

a rectangular cuff;

a fastening material placed on one end of said rectangular cuff;

a mating fastening material placed on another end of said rectangular cuff, said mating fastening material adapted to attach to said fastening material;

a pair of electrodes positioned a predetermined distance apart and held by said rectangular cuff;

a control unit placed on said rectangular cuff and attached to said pair of electrodes;

a door placed on said control unit, said door covering controls for the frequency, the repetition, and the interval; and a power source attached to said control unit, whereby a user can attach and position the device easily and apply a safe and effective electrical signal causing muscle contraction.

9. A self applied device for use in preventing circulatory ailments comprising:

a rectangular cuff;

a fastening material placed on one end of said rectangular cuff;

a mating fastening material placed on another end of said rectangular cuff, said mating fastening material adapted to attach to said fastening material;

a pair of electrodes positioned a predetermined distance apart and held by said rectangular cuff, said pair of electrodes comprise disposable electrodes;

a control unit placed on said rectangular cuff and attached to said pair of electrodes; and a power source attached to said control unit, whereby a user can attach and position the device easily and apply a safe and effective electrical signal causing muscle contraction.

10. An electrical device for use in preventing circulatory ailments comprising:

a pair of electrodes;

signal means, attached to said pair of electrodes, for providing a signal to said pair of electrodes having a form of substantially a square wave with an intensity of between 1 to 20 milliamperes, a duration of between 0.1 and 0.3 milliseconds, a frequency of between 0.1 and 0.5 Hertz, with 5 to 15 repetitions delivered every 5 to 15 minute intervals.

11. An electrical device for use in preventing circulatory ailments as in claim 10 further comprising:

a cuff having attached thereto said pair of electrodes and said signal means.

12. An electrical device for use in preventing circulatory ailments as in claim 11 further comprising:

a fastener placed on said cuff, whereby said cuff is releasably attachable to the leg of a user.

13. An electrical device for use in preventing circulatory ailments as in claim 12 further comprising:

indicia placed on said cuff, said indicia located to assist.

14. An electrical device for use in preventing circulatory ailments as in claim 13 wherein:

said indicia comprises a line placed midway between said pair of electrodes.

15. A method for preventing circulatory ailments comprising the step of:

applying an electrical signal to the leg of a user with an intensity of between 1 to 20 milliamperes, a duration of between 0.1 and 0.3 milliseconds, a frequency of between 0.1 and 0.5 Hertz, with 5 to 15 repetitions delivered every 5 to 15 minute intervals.

16. A method for preventing circulatory ailments as in claim 15 wherein:

the step of applying an electrical signal comprises applying substantially a square wave.

17. A method for preventing circulatory ailments as in claim 16 wherein:

the step of applying an electrical signal comprises applying a asymmetrical by-phasic pulse.

18. A self applied device for use in preventing circulatory ailments such as deep vein thrombosis or pulmonary emboli, venostasis, ankle edema and leg discomfort associated with prolonged sitting comprising:

an elongated rectangular cuff;

two straps attached to one side of one end of said elongated rectangular cuff, each of said two straps having a first type of fastening material thereon;

a first patch of fastening material placed between said two straps and on the other side of said elongated rectangular cuff on the one end, said first patch of fastening material made of a second type of fastening material, the second type of fastening material attaching to the first type of fastening material upon contact;

two strips attached to the other end of said rectangular cuff on the one side, each of said two strips having the second type of fastening material thereon;

a second patch of fastening material placed between said two strips, said second patch of fastening material made of a first type of fastening material, the first type of fastening material attaching to the second type of fastening material upon contact;

a pair of disposable electrodes positioned approximately twelve centimeters apart and attached to said elongated rectangular cuff;

a control unit placed on said rectangular cuff and attached to said pair of electrodes, said control unit providing an electrical signal to said electrodes having a form of substantially an asymmetrical bi-phasic square pulse with an intensity of between 1 to 20 milliamperes, a duration of between 0.1 and 0.3 milliseconds, a frequency of between 0.1 and 0.5 Hertz, with 5 to 15 repetitions delivered every 5 to 15 minute interval;

a single external user accessible intensity control placed on said control unit; and a battery attached to said control unit, whereby a user can attach and position the device easily and apply a safe and effective electrical signal causing muscle contraction.

* * * * *